United States Patent [19]

Dankowski et al.

[11] Patent Number: 4,874,556
[45] Date of Patent: Oct. 17, 1989

[54] PROCESS FOR THE DESENSITIZATION OF WATER-INSOLUBLE PEROXYCARBOXYLIC ACIDS

[75] Inventors: Manfred Dankowski, Moembris-Koenigshofen; Willi Hofen, Rodenbach, both of Fed. Rep. of Germany

[73] Assignee: Degussa Aktiengesellschaft, Frankfurt am Main, Fed. Rep. of Germany

[21] Appl. No.: 266,237

[22] Filed: Oct. 28, 1988

Related U.S. Application Data

[63] Continuation of Ser. No. 63,045, Jun. 17, 1987, abandoned.

[30] Foreign Application Priority Data

Aug. 25, 1986 [DE] Fed. Rep. of Germany ....... 3628263

[51] Int. Cl.$^4$ .................................. C07C 179/133
[52] U.S. Cl. .................................. 562/2; 562/3
[58] Field of Search .................................. 260/502 R

[56] References Cited

FOREIGN PATENT DOCUMENTS 0045290 2/1982 European Pat. Off. ........ 260/502 R
0127783 12/1984 European Pat. Off. ........ 260/502 R Primary Examiner—Bruce Gray
Attorney, Agent, or Firm—Beveridge, DeGrandi & Weilacher

[57] ABSTRACT

A process for desensitization of water insoluble peroxycarboxylic acids with essentially sodium sulfate in the aqueous phase, wherein the desensitized peroxycarboxylic acids is separated from the mother liquor, and the sodium sulfate contained in the mother liquor is isolated by one- or multi-stage crystallization in purified form as the deca (hepta) hydrate and this, directly or after conversion to an aqueous sodium sulfate solution, and/or anhydrous sodium sulfate is returned to the desensitization process. The process is nonpolluting and can be operated safely on the industrial scale. The peroxycarboxylic acids desensitized according to the invention are characterized by lower heavy metal content and high storage stability.

12 Claims, No Drawings

PROCESS FOR THE DESENSITIZATION OF WATER-INSOLUBLE PEROXYCARBOXYLIC ACIDS

This is a continuation of our application Ser. No. 063,045 filed June 17, 1987, now abandoned.

The present invention relates to a process for the desensitization of water insoluble peroxycarboxylic acids with sodium sulfate as the essential desensitizing agent, wherein sodium sulfate dissolved in the mother liquor is recycled in purified form back to the process.

Peroxycarboxylic acids are used not only as oxidizing agents in organic syntheses, but also as bleaching active components in washing and cleansing compositions, especially such compositions intended for use with textiles, since the action of these acids occurs below 80° C. See for example, European Pat. No. A1 0 037 146, U.S. Pat. No. 4,119,660.

Various processes have been previously described for synthesis of aliphatic or aromatic mono- and diperoxycarboxylic acids which are solid at room temperature and insoluble or slightly soluble in water. Peroxycarboxylic acids can be synthesized, for example, from the corresponding carboxylic acids with aqueous hydrogen peroxide in the presence of sulfuric acid and an organic solvent; in a discontinuous manner as shown in U.S. Patent 4,172,086, or is a continuous manner as shown in European Patent B1 0 045 290.

In the absence of an organic solvent, peroxycarboxylic acids can be synthesized by peroxidizing with hydrogen peroxide, for example according to U.S. Pat. No. 4,233,235, aliphatic dicarboxylic acids dissolved in concentrated sulfuric acid or, for example according to U.S. Pat. No. 4,244,884; West German DE-OS No. 33 20 497 (U.S. Ser. No. 615,303 filed May 30, 1984) or West German DE-OS No. 34 18 450, aliphatic or aromatic carboxylic acids suspended in sulfuric acid. Instead of the carboxylic acids, sometimes also the anhydrides thereof, see West German DE-OS No. 34 38 529, can be peroxidized with hydrogen peroxide in the presence of sulfuric acid.

Since solid, water insoluble peroxycarboxylic acids in pure or highly concentrated condition are thermally and mechanically sensitive, in connection with the synthesis thereof attention has also been paid to desensitization or stabilization. According to Belgian Patent 560,389, desensitization or stabilization can be achieved in particular by addition of such alkali, alkaline earth as well as earth metal salts of strong mineral acids that bind water of crystallization, especially sodium sulfate, magnesium sulfate, disodium orthophosphate, disodium tetraborate, aluminum sulfate.

For safety related reasons, however, the mixing of highly concentrated peroxycarboxylic acids with the corresponding desensitizing agents is not without problems. More advantageous in contrast thereto are processes in which the desensitizing agent is formed in situ following the peroxycarboxylic acid synthesis in the presence of sulfuric acid by neutralization of the same with alkali or alkaline earth metal hydroxides or alkali metal aluminates or alkali metal borates, see U.S. Pat. No. 4,287,135; West German DE-OS No. 33 20 496; European Pat. No. B1 00 45 290. The desensitization of peroxycarboxylic acids with in situ formation of the very effective desensitization agent, sodium sulfate which does not interfere in the use in bleaching and cleansing agents, can be achieved below the temperature of transformation of sodium sulfate decahydrate to thenardite, see U.S. Pat. No. 4,287,135, and also above this temperature, which is more advantageous in regard to simpler drying of the thusly desensitized peroxycarboxylic acids, see West German DE-OS No. 33 20 496; European Pat. No. B1 00 45 290.

In all processes for desensitization of water insoluble peroxycarboxylic acids using essentially sodium sulfate as the desensitizing agent in the aqueous phase, there is obtained, after separation of the desensitized peroxycarboxylic acids, a mother liquor, which is saturated with sodium sulfate and contains water soluble impurities. In the past, the brine solutions produced in peracid synthesis processes have usually been discarded. However, processes for desensitization of peroxycarboxylic acids can be economically carried out and the established requirements of environmental protection complied with only if no sodium sulfate containing mother liquor is required to be disposed of, and instead, the sodium sulfate dissolved in the mother liquor is recycled to the process.

Accordingly, European Pat. No. B1 0045 290 is directed toward a continuous process for the synthesis of peroxycarboxylic acid compositions from the corresponding carboxylic acids and aqueous hydrogen peroxide in the presence of a concentrated strong acid and an organic solvent and using sodium sulfate as well as boric acid as desensitizing agent. In the described process the mother liquor is recycled. In this known process, the desensitizing agent is formed in situ from the sulfuric acid present in the system by addition of borax and a source for the soda. This in situ reaction is able to occur either during the desensitization, that is to say, before the separation of the desensitized peroxycarboxylic acids from the mother liquor, or, after this separation, in the mother liquor, which in this case still contains sulfuric acid. In the first embodiment, the mother liquor saturated with sodium sulfate and boric acid and, after any necessary evaporation, also containing crystals, is entirely recycled for dilution of the sulfuric acid mixture containing the peroxycarboxylic acids. In the second embodiment, the crystal suspension containing the crystallized desensitizing agent formed by neutralization of the mother liquor is recycled.

In the prior art processes cited above, all impurities dissolved in the aqueous mother liquor as well as occasionally undissolved impurities entrained in the form of finely divided strained substances during separation of the desensitized peroxycarboxylic acids are recycled with the mother liquor and possibly even concentrated by partial evaporation.

The impurities present in these prior known processes are impurities introduced with the starting materials used for peroxycarboxylic acid synthesis and/or for desensitization and/or processing auxiliaries present in low concentration and possibly interfering in the end product. In addition, impurities as introduced which are formed by the chemical reaction or in a material related manner during the synthesis and/or desensitization processes.

The prior art processes at no point provide for purification of the mother liquor. Moreover, the water content of the process is controlled by very expensive evaporation. Consequently, a higher impurity level builds up progressively in the system. Thus, an unwanted decomposition, catalyzed by these impurities, of the peroxycarboxylic acids in the desensitization stage must be reckoned with and can no longer be ruled out. Considered from the safety related viewpoint, such a process, at least if the intention is to conduct it on the industrial scale, is risky or even prohibitive, even if a partial stream is removed from the mother liquor prior to recycling.

Another disadvantage of known methods is that peroxycarboxylic acids desensitized according to this known process necessarily have a higher degree of contamination, which based on practical experience, leads to poorer storage stability.

The object of the present invention is accordingly to provide a method for desensitization or stabilization of water insoluble peroxycarboxylic acids with essentially sodium sulfate as the desensitizing agent in the aqueous phase and with recycling of the sodium sulfate dissolved in the mother liquor.

It is a further object of the present invention to provide a method which does not have the disadvantages of the prior art processes but keeps the impurity level low by a purification integrated into the process and thus permits the process to be carried out safely and in a technically simple manner even on the industrial scale and which method leads to a product having good storage stability.

In attaining these and other objects, a feature of the present invention resides in a process for the desensitization of water insoluble peroxycarboxylic acids with essentially sodium sulfate as the desensitizing agent, comprising bringing the peroxycarboxylic acids into contact with the desensitizing agent in the aqueous phase, separating the desensitized peroxycarboxylic acids from the mother liquor in any known manner, if necessary, conditioning before drying, and returning the sodium sulfate dissolved in the mother liquor to the process. Heat is withdrawn from the mother liquor after separation of the desensitized peroxycarboxylic acids for crystallization of sodium sulfate decahydrate and possibly also sodium sulfate heptahydrate. The crystallized sodium sulfate hydrates are separated from the spent liquor containing the impurities and at least part of the separated sodium sulfate hydrates themselves or after conversion of the same to an aqueous solution and/or anhydrous sodium sulfate is returned by recycling to the process.

In the process of the present invention, after separation of the desensitized peroxycarboxylic acids by conventional means, for example, filtering or centrifuging, a mother liquor is obtained which is generally saturated with sodium sulfate and which also contains the raw-material-, process and equipment-related impurities essentially dissolved in the mother liquor. The separation may be done by any suitable method. By continuous or stepwise cooling of the mother liquor to temperatures below 32.4° C., the temperature of transformation of thenardite to sodium sulfate decahydrate, sodium sulfate decahydrate crystallizes out and, at lower temperatures, especially below approximately 12° C., so also does the less stable sodium sulfate heptahydrate. The heptahydrate crystal forms transforming readily to the decahydrate in the presence of moisture, see Ullmanns Enzyklopaedie der technischen Chemie (Encyclopedia of Industrial Chemistry), Vol. 12, page 682, Urban and Schwarzenberg, 1960. Below the cryohydric point of the aqueous mother liquor containing sodium sulfate, which point is a few degrees below 0° C. depending on the presence and concentration of further dissolved constituents, no additional sodium sulfate decahydrate/heptahydrate precipitates out.

After separation of the crystallized sodium sulfate hydrates by filtering or centrifuging there is obtained a spent liquor which, depending on crystallization conditions, is strongly depleted of sodium sulfate down to 3 to 5 weight percent of sodium sulfate and heavily enriched with impurities. This spent liquor, which in addition to small quantities of sodium sulfate and the impurities possibly also contains some hydrogen peroxide, sulfuric acid and Caro's acid as well as dissolved peroxycarboxylic acids and/or traces thereof entrained during the separation, can in general be fed directly to a biological clarifying stage and disposed of therein by conventional methods.

The sodium sulfate hydrates obtained during the crystallization in accordance with the present invention—meaning the decahydrates as well as the poorly stable heptahydrate—are sufficiently pure after separation thereof from the mother liquor. Without risk of catalytic decomposition of the active oxygen; i.e., the hydrogen peroxide, the Caro's acid and/or peroxycarboxylic acids, or impairment of the storage stability of the desensitized peroxycarboxylic acids, the thusly purified sodium sulfates can be returned to the process directly or after the conversion thereof to an aqueous, especially saturated solution and/or anhydrous sodium sulfate. Thus, not only is the sodium sulfate dissolved in the mother liquor returned to the process, but also practically all impurities present in the desensitization process, including even the particularly critical heavy metal traces, are discharged from the system with the easily disposable spent liquor.

The process of the present invention, comprising the steps of crystallization and recycling of the sodium sulfate originally dissolved in the mother liquor, is suitable for desensitization of peroxycarboxylic acids synthesized by known methods, especially those cited in the technical literature. Therefore, peroxycarboxylic acids which are first isolated and possibly still filter damp can be brought into contact with sodium sulfate, part of which is obtained from the sodium sulfate hydrates crystallized from the mother liquor, and thereafter be separated as desensitized peroxycarboxylic acids from the mother liquor. In addition, and even preferably so, such peroxycarboxylic acids which are still present in the aqueous reaction mixture from the synthesis thereof can also be handled in this way.

It is quite particularly advantageous to bring the peroxycarboxylic acids after their synthesis from the corresponding carboxylic acids or anhydrides and hydrogen peroxide in the presence of sulfuric acid, possibly organic solvents and processing auxiliaries directly into contact with sodium sulfate in the aqueous phase of the reaction mixture, which also contains sulfuric acid, before or after separation of any organic solvent which is present. In so doing, at least part of the sodium sulfate necessary for the desensitization is produced by in situ formation from the sulfuric acid present in the system and an alkaline acting sodium compound, preferably sodium hydroxide, and at least part of the sodium sulfate being sodium sulfate recycled according to the invention. In this embodiment, sodium sulfate hydrates isolated from the mother liquor, preferably in the form of a saturated aqueous solution, are passed into the aqueous sulfuric acid reaction mixture containing the peroxycarboxylic acids, and thereafter the sulfuric acid is converted to sodium sulfate by neutralization to a pH of 2 to 6.

With the process of the present invention, it is possible in a technically simple and safe manner to desensitize, using essentially sodium sulfate, peroxycarboxylic acids before or after separation thereof from the reaction mixture of the synthesis thereof. The term "essentially sodium sulfate" as used herein means that other known desensitizing agents known for peroxycarboxylic acids, especially boric acid, alkali, alkaline earth and earth metal sulfates, can also be present, in smaller quantities than the sodium sulfate. The person skilled in the art will be able to readily determine by simple tests the quantity which can be used of these other desensitizing agents without disturbing the process of the present invention as regards safety of the process and stability of the other product. Whether, or to what extent these additional materials also crystallize out during the crystallization of the sodium sulfate hydrates and/or whether the spent liquor must be post treated before disposal thereof will be matters well within the scope of those skilled in the art.

The invention is suitable for the desensitization of water insoluble aromatic and aliphatic peroxycarboxylic acids, especially monoperoxy- and diperoxycarboxylic acids, which are derived from aliphatic straight chain or branched mono- or dicarboxylic acids with 6 to 20, preferably 7 to 14 carbon atoms or aromatic mono- and dicarboxylic acids with 7 to 12 carbon atoms, especially benzene- and naphthalene dicarboxylic acids.

The term "water insoluble" as used therein is intended to mean peroxycarboxylic acids which have a water solubility of less than approximately 5.0 weight percent. Especially preferred are aliphatic alpha, omega-diperoxycarboxylic with 10 to 14 carbon atoms, especially diperoxy acid.

The peroxycarboxylic acids are brought into contact in the aqueous phase with such a quantity of sodium sulfate that the desensitized peroxycarboxylic acids thereafter separated in conventional manner from the mother liquor and dried in conventional manner, preferably 30° C. to 60° C., contain approximately 3 to 90 weight percent of sodium sulfate. Preferably, the desensitization is carried out in the presence of sodium sulfate dissolved in the aqueous phase and suspended therein. The suspended sodium sulfate can in this case be added as raw material and/or have been formed in situ during the desensitization from present sulfuric acid present in the system and/or can be recycled sodium sulfate obtained from the mother liquor.

The desensitization and separation of the desensitized peroxycarboxylic acids from the mother liquor is carried out preferably at temperatures above 32.4° C. and below such temperatures at which marked decomposition of the peroxycarboxylic acids occurs, preferably below 45° C. In the preferred embodiment at temperatures between 32.4° C. and 45° C., the desensitizing agent exists as thenardite, and drying of the peroxycarboxylic acids, which, if necessary, are also conditioned beforehand, causes no difficulties. In contrast, if the desensitized peroxycarboxylic acids are separated at temperatures below the temperature of transformation of thenardite to sodium sulfate decahydrate, precise adjustment of the content of desensitizing agent is rendered difficult because of the possible supersaturation as well as drying may cause problems.

The crystallization of the sodium sulfate hydrates from the mother liquor is carried out, preferably in a manner specially adapted to this crystallization and in an apparatus suitable therefor. The solubility of sodium sulfate in water decreases so steeply in the range from approximately 32° C. to approximately 10° C. that, as a result of strong supersaturation, for example at the cooling walls of a heat exchanger, incrustations are formed due to the high growth speeds and large nucleation rates. Even at flow velocities of 2 m/sec and higher in the heat exchanger, such incrustations on tube walls of normal roughness are still possible.

It has now been found that these difficulties can be overcome by effecting, preferably in the upper temperature range down to approximately $+10°$ C., the removal of the heat of crystallization and reduction of the temperature of the mother liquor by evaporative cooling in vacuum in one or more stages, discontinuously or continuously. That is, by cooling down to about 10° C. employing evaporative cooling means, the incrustation problems encountered previously when using conventional tube bundle heat exchanger can be avoided. By means of suitable vacuum generation, the pressure in the crystallization tank, which preferably is equipped with a reflux condenser, is reduced in steps and the mother liquor is thus made to boil; as a result, the temperature drops very rapidly and Glauber's salt essentially precipitates out.

However, in the lower temperature range, preferably from approximately $+10°$ C. down to 0° C., close to the cryohydric point, the heat is withdrawn from the mother liquor preferably by heat exchangers. This is able to be carried out without danger of incrustation with sufficiently smooth heat exchanger surfaces, for example polished stainless steel or enamel tubes, and sufficiently high flow velocity. It is important in this respect that the surface of the heat exchanger conform to this desired degree of smoothness, but the actual structure of the heat exchanger is conventional. The cooling and thus the crystallization speed is preferably controlled in such a way that the crystallized sodium sulfate hydrates include practically no mother liquor and thus no impurities.

In another preferred embodiment, the heat is withdrawn from the mother liquor initially in the upper temperature range, by evaporative cooling in vacuum, and thereafter in the lower temperature range, by activating heat exchangers having the above-mentioned smooth surfaces.

The discontinuous cooling crystallization by evaporative cooling, if necessary in combination with heat exchangers, is effected by one, two, or more stages. In the multi-stage mode of operation, the temperature of the mother liquor, saturated with sodium sulfate and separated, for example above 32.4° C., from the desensitized peroxycarboxylic acids is lowered in the first stage to approximately 25° to 27° C., the crystal containing suspension is separated, preferably in a centrifuge, and the mother liquor depleted of sodium sulfate is fed to the second stage. The second stage of cooling and crystallization is terminated at approximately 15° C. Then the mother liquor after separation is cooled in a third stage to about 0° C., from approximately 10° C., the heat being removed from the system preferably by heat exchangers. The mother liquor obtained after the third stage after separation can be disposed of without problems, for example, in a biological clarifying plant.

A third stage can be dispensed with if, during the second stage, further depleted mother liquor or spent liquor is add for sufficient dilution of the crystal suspension being formed by cooling, and then cooling is effected to 0° C. or below.

If provision for continuous discharge of crystals is made during the phase of cooling of the mother liquor, perhaps by means of a suspension discharge pump, cooling can be carried out continuously in one stage to below 0° C. From approximately +10° C., it is recommended that the heat be removed by effective heat exchangers, since at low temperatures, cooling by vacuum boiling is no longer economically attractive.

In another embodiment which is particularly preferred for continuous desensitization on the industrial scale, the sodium sulfate hydrates are crystallized continuously at approximately constant temperature, preferably below +10° C. and above the cryohydric point and quite especially at approximately 0° C. A mother liquor saturated at higher temperature is added continuously to and the resulting crystal suspension being withdrawn continuously from the crystallization tank, which is equipped with effective cooling devices and in which a mother liquor saturated with sodium sulfate at the crystallization temperature is originally present. The crystallized salt is separated from the spent liquor by centrifuging or filtering.

In order to modify the rheological properties of the crystal suspension with regard to better handling and, if necessary, to reduce the caking tendency of the separated sodium sulfate hydrates, it is possible during the crystallization thereof to use crystallization auxiliaries in small quantities, provided these do not interfere with the actual desensitization process and the desensitized peroxycarboxylic acids. The skilled worker in the field will be able to test such auxiliaries for the suitability thereof in preliminary tests. Surface active agents can be used for this purpose and, for example, ammonium salts of inorganic acids or products of addition of ethylene oxide and saturated $C_{12-18}$ alcohols or amides of $C_{12-18}$ fatty acids. Such materials are well known in the art.

The Glauber's salt (sodium sulfate decahydrate, possibly with portions of sodium sulfate heptahydrate) isolated from the mother liquor is very pure and contains less than 4 ppm of Fe and less than 1 ppm of Cu.

When the desensitization process of the present invention is carried out in the aqueous sulfuric acid phase of a reaction mixture following conventional peroxycarboxylic acid synthesis using commercially available raw materials, the spent liquor depleted of sodium sulfate contains generally more than 4 ppm of Fe and more than 1 ppm of Cu.

The impurities contained in the spent liquor and especially the critical heavy metal traces dissolved therein are, in the process of the present invention, completely withdrawn from the system and thus represent no safety risk. This is in stark contrast to the heretofore conventional processes wherein the impurity level constantly increases due to the recycling of the mother liquor, and a safe operation could not be incurred.

Also in the process of the present invention, in contrast to the prior art process, a thermal load on the mother liquor, which still contains active oxygen, does not occur.

The heavy metal content of the desensitized peroxycarboxylic acids of the invention is generally lower than 2 ppm.

Even after a five fold recycling of the entire sodium sulfate isolated from the mother liquor, the desensitized peroxycarboxylic acids have heavy metal contents of generally well below 5 ppm.

The storage stability of the desensitized peroxycarboxylic acids of the invention is essentially not altered by the recycling of the sodium sulfate and corresponds to that of such products which are desensitized in the aqueous phase without recycling of the mother liquor.

The salt, essentially sodium sulfate decahydrate, separated from the spent liquor can be returned directly to the desensitization. However, it is advantageous to convert this salt beforehand by melting, preferably at 32.4° C. to 45° C., to an aqueous solution saturated with sodium sulfate and anhydrous sodium sulfate suspended therein. After separation of the solid from the liquid phase by centrifuging or filtering or other means, at least part of the solution and/or at least part of the anhydrous sodium sulfate is returned to the desensitization process. This process step is especially advantageous when the intention is to desensitize peroxycarboxylic acids above 32.4° C. in an aqueous sulfuric acid phase, as exists in known peroxycarboxylic acid synthesis processes after completion of peroxidation, with in situ formation of sodium sulfate. The saturated solution obtained by melting of the crystallized sodium sulfate hydrates of the invention and freed of undissolved $Na_2SO_4$ is in this case added for dilution to the aqueous sulfuric acid phase containing peroxycarboxylic acids. After this sodium sulfate is formed in situ in a known manner by neutralization of the sulfuric acid with an alkaline-acting sodium compound, preferably sodium hydroxide. The desensitized peroxycarboxylic acids obtained thereby are conditioned as necessary with anhydrous sodium sulfate obtained from mother liquor reprocessing. This conditioning can be effected before or after the separation of the desensitized peroxycarboxylic acids from the mother liquor, conditioning before separation being preferred. The term "contitioning" as used herein signifies the precise control of the degree of desensitization of the acids through mixing of the sodium sulfate with the acids to be desensitized.

It is characteristic of the procedure described above that the aqueous sulfuric, acid reaction medium containing the water insoluble peroxycarboxylic acids is diluted sufficiently with recycled $Na_2SO_4$ solution before the exotheric in situ formation of sodium sulfate. In this case, not only is the viscosity of the suspension reduced, but also the removal of the heat of neutralization is facilitated. As a result, the process can be carried out more simply and in particular more safely. Following the neutralization and preferably before the separation of the desensitized peroxycarboxylic acids, the anhydrous sodium sulfate obtained from mother liquor reprocessing can then be mixed entirely or partly for conditioning, i.e., for precise adjustment of the desired degree of desensitization.

The technical improvement of the process of the invention lies in the fact that it is now possible, for the first time, to process the aqueous mother liquor obtained from the desensitization of peroxycarboxylic acids in such a way that the sodium sulfate dissolved therein is returned in purified form to the desensitization treatment, and the process can be operated in a technically simpler and especially safer manner, even on the industrial scale, and only a small amount of polluting spent liquor must be disposed of.

The invention will be explained in greater detail with reference to the examples.

EXAMPLE 1

Reprocessing of a mother liquor from the synthesis and desensitization of diperoxycarboxylic acid (DPDDA) according to Example 6 of West German DE-OS No.33 20 497, corresponding to U.S. Ser. No. 615,303, filed May 30, 1984 viz:

In an oxidation mixture formed of 102 g. hydrogen peroxide (50 wt %), 204 g. sulfuric acid (96 wt %) and 25 g. sodium sulfate solution (13 wt %) and 1.6 g. tri-n-octyl phosphane oxide, there is introduced 115 g. dodecandioic acid. The mixture was heated with stirring for 8 hours at 60° C. After cooling to 40° C., the reaction mass is treated with 263 g. sodium sulfate solution (30 wt %) and subsequently neutralized with 526 g. sodium hydroxide solution (30 wt %) until a pH value of 3.5 is obtained. It is then conditioned with 160 g. solid sodium sulfate. Following that, the mass is centrifuged and dried. The yield of the peracids is 118.3 g.≗90.3% of theory.

The total AO content was found to be 4.25%.
The dodecanedioic acid balance was 97.5%.
Content of DPDDA was 34.4%.

The entire disclosure of U.S. Ser. No. 615,303 is incorporated herein and relied on.

There is charged into the tank of a crystallization system, equipped with an effective reflux condenser, a suspension recirculation pump, devices for vacuum generation, an external tubular heat exchanger with cooling means, a suspension discharge pump as well as the necessary feed and discharge pipes and safety devices, 161 kg of mother liquor to be reprocessed, saturated with sodium sulfate at 40° C., also containing small quantities of hydrogen peroxide, sulfuric acid and possibly Caro's acid and impurities from the process. By means of a vacuum pump the pressure in the system is reduced in steps until the mother liquor, at a temperature f approximately 40° C., begins to boil and a condensate reflux is produced in the condenser; at this time, the external heat exchanger is not yet in operation. During the temperature drop which now begins, a crystal suspension, which is kept from settling by the suspension recirculation pump, is formed in the crystallization tank. By means of a suspension discharge pump, the crystal suspension is passed continuously to a centrifuge and therein the crystals are separated from the mother liquor, which is now depleted of sodium sulfate and which is collected in an intermediate tank and pumped therefrom back to the crystallization tank. The intermediate tank is a conventional piece of equipment that merely acts to store the mother liquor. From approximately 10° C. the external heat exchanger, which is cooled with a refrigerant, is activated and the temperature is lowered further to about 0° C. by recirculating the crystal suspension through the heat exchanger. The flow velocity in the smooth tubes of the heat exchanger is 2 m/sec.

At the end of crystallization, 438 kg of sodium sulfate decahydrate, possibly with some heptahydrate, is obtained in the centrifuge. A total of 133 kg of spent liquor with about 4 weight percent sodium sulfate, as well as the concentrated impurities, is obtained in the intermediate tank and crystallization tanks.

EXAMPLE 2

Conversion of the sodium sulfate decahydrate to a saturated solution and anhydrous sodium sulfate:

There is charged into a heatable melting tank equipped with conventional mixing means 483 kg of the sodium sulfate decahydrate recovered in Example 1 from a mother liquor. Melting is carried out at approximately 40° C. The resulting suspension is fed by a discharge pump to a centrifuge. After separation there is obtained 413 kg of saturated pure sodium sulfate solution and 70 kg of pure anhydrous $Na_2SO_4$ (solid).

EXAMPLE 3

Desensitization of diperoxydodecanedioic acid 54 kg of dodecanedioic acid is metered into an oxidation mixture, consisting of 48 kg of hydrogen peroxide (50 weight percent), 96 kg. sulfuric acid (96 weight percent) and 11 kg of recycled sodium sulfate solution (6 weight percent), as well as 0.15 kg of tri-n-octylphosphane oxide, and heating is effected for 2 to 6 hours with stirring at 60° C.

After cooling to 40° C., the preparation is mixed at this temperature with 260 kg of a sodium sulfate solution (30 weight percent) obtained according to Example from a previous preparation, followed by neutralization with 250 kg of sodium hydroxide solution (30 weight percent) until a pH of 3.5 is reached, whereupon conditioning is effected with 71 kg of recycled anhydrous sodium sulfate, obtained according to Example 2 from a previous preparation. This is followed by separation and drying. The desensitized 35 weight percent peracid is obtained in a yield of 90%.

Further modification and variations of the present invention will be apparent to those skilled in the art and are intended to be encompassed by the claims appended hereto.

German priority application P 36 28 263.4-42, is incorporated herein by reference.

We claim:

1. A process for the desensitization of water insoluble peroxycarboxylic acids with essentially sodium sulfate as the desensitizing agent, comprising contacting said peroxycarboxylic acids in the absence of an organic solvent with the desensitizing agent in the aqueous phase, which is essentially sodium sulfate to thereby obtain the desensitized peroxycarboxylic acids, separating said acids from mother liquor that is formed thereby, withdrawing heat from said mother liquor after separation of the desensitized peroxycarboxylic acids to thereby crystallize pure sodium sulfate in the form of the decahydrate or heptahydrate or mixtures thereof, separating the crystallized sodium sulfate hydrates free of impurities from the spent liquor which contained the impurities present in the desensitization process and is discharged from the system and returning at least part of the separated sodium sulfate to the process for contacting with untreated peroxycarboxylic acids.

2. The process according to claim 1 wherein the impurities including critical heavy metal traces are discharged with the spent liquor.

3. The process according to claim 1 wherein the peroxycarboxylic acids are contacted with sodium sulfate in the aqueous phase, said aqueous phase containing sulfuric acid, at least part of the sodium sulfate necessary for desensitization being produced by in situ formation from the sulfuric acid present and an alkaline acting sodium compound.

4. The process as set forth in claim 1, wherein water insoluble monoperoxy- or diperoxycarboxylic acids derived from aliphatic or aromatic mono- or dicarboxylic acids are desensitized.

5. The process as set forth in claim 1, wherein the peroxycarboxylic acids are brought into contact with such a quantity of sodium sulfate that after the separation from the mother liquor, the separated peroxycarboxylic acids are dried and contain approximately 3 to 90 weight percent of sodium sulfate.

6. The process as set forth in claim 1, wherein the desensitization and separation of the desensitized peroxycarboxylic acids from the mother liquor are carried out at temperatures above the temperature of transformation of sodium sulfate decahydrate to thenardite and below such temperatures, at which marked decomposition of the peroxycarboxylic acids occurs.

7. The process as set forth in claim 3, wherein the sodium compound is sodium hydroxide.

8. The process as set forth in claim 1, further comprising withdrawing heat from the mother liquor by evaporating cooling in vacuum to thereby obtain crystallization of the sodium sulfate hydrate.

9. The process as set forth in claim 1, wherein, in the temperature range of from approximately $+10°$ C. to below $0°$ C., close to the cryohydric point of the crystals, heat is withdrawn from the mother liquor by heat exchangers for crystallization of the sodium sulfate hydrates.

10. The process as set forth in claim 1, wherein the crystallization of the sodium sulfate hydration from the mother liquor is carried out at a substantially constant temperature in the range of below $+10°$ C. and above the cryohydric point of the crystals, by continuously feeding mother liquor saturated with sodium sulfate above the crystallization temperature to the crystallization zone equipped with an effective evaporative cooling means and/or heat exchangers, and containing a mother liquor approximately saturated with sodium sulfate at the chosen crystallization temperature, and continuously withdrawing formed sodium sulfate decahydrate and/or sodium sulfate heptahydrate crystal suspension and separating the crystals from the spent liquor.

11. The process as set forth in claim 1, wherein the sodium sulfate hydrates separated from the spent liquor are converted by melting at or above the temperature of transformation of the sodium sulfate decahydrate to thenardite, to a solution saturated with sodium sulfate and anhydrous sodium sulfate suspended therein, the suspended sodium sulfate is separated from the solution and at least part of the solution and/or of the anhydrous sodium sulfate is returned to the desensitization process.

12. The process as set forth in claim 3, wherein the solution saturated with sodium sulfate obtained from the sodium sulfate hydrates separated from the spent liquor and converted by melting at or above the temperature of transformation of the sodium sulfate decahydrate to thenardite, is added to the aqueous sulfuric acid phase containing the peroxycarboxylic acids to be desensitized, the sulfuric acid is converted to sodium sulfate and the anhydrous sodium sulfate obtained from the sodium sulfate hydrate is added entirely or partly for conditioning of the desensitized peroxycarboxylic acids before or after separation of the same from the mother liquor.

* * * * *